(12) United States Patent
Schmidt

(10) Patent No.: US 8,946,399 B2
(45) Date of Patent: Feb. 3, 2015

(54) PATHOGEN-INDUCIBLE SYNTHETIC PROMOTER

(75) Inventor: Klaus Schmidt, Lahstedt/Gr. Lafferde (DE)

(73) Assignee: KWS SAAT AG, Einbeck (DE)

( * ) Notice: Subject to any disclaimer, the term of this patent is extended or adjusted under 35 U.S.C. 154(b) by 1062 days.

(21) Appl. No.: 12/299,306

(22) PCT Filed: Jun. 16, 2007

(86) PCT No.: PCT/DE2007/001075
§ 371 (c)(1),
(2), (4) Date: Nov. 1, 2008

(87) PCT Pub. No.: WO2007/147395
PCT Pub. Date: Dec. 27, 2007

(65) Prior Publication Data
US 2009/0188006 A1 Jul. 23, 2009

(30) Foreign Application Priority Data

Jun. 22, 2006 (DE) .......... 10 2006 029 129

(51) Int. Cl.
| | | |
|---|---|---|
| C12N 15/63 | (2006.01) | |
| C12N 15/82 | (2006.01) | |
| C12N 15/87 | (2006.01) | |
| A01H 5/00 | (2006.01) | |
| C07K 14/415 | (2006.01) | |

(52) U.S. Cl.
CPC .......... *C12N 15/8239* (2013.01); *C07K 14/415* (2013.01)
USPC ........ 536/24.1; 435/320.1; 800/279; 800/287

(58) Field of Classification Search
USPC ....................................... 536/24.1
See application file for complete search history.

(56) References Cited

U.S. PATENT DOCUMENTS 5,689,044 A * 11/1997 Ryals et al. .................. 800/301
6,605,764 B1   8/2003 Chappell et al.

FOREIGN PATENT DOCUMENTS

| WO | 9319188 A1 | 9/1993 |
|---|---|---|
| WO | 9803536 A1 | 1/1998 |
| WO | 0029592 A2 | 5/2000 |
| WO | 03083042 A2 | 10/2003 |
| WO | 2005063994 A1 | 7/2005 |
| WO | 2005123919 A1 | 12/2005 |

OTHER PUBLICATIONS

Hooft et al. 1986, EMBO 5:2057-2061.*
Database EMBL [Online]:"Solanum tuberosum disease resistance homolog gene, clone 32", abstract, XP002463671, Dec. 14, 1996.
Leister, D. et al.:"A PCR-based approach for isolating pathogen resistance genes from potato with potential for wide application in plants", Nature Genetics, New York, NY, US, vol. 14, pp. 421-429, XP000964717, Dec. 1996.
Database EMBL [Online]:"Zea mays PR4 gene promoter", abstract, XP002474396, May 8, 2005.
Moreno, Ana Beatriz et al.:"Pathogen-induced Production of the Antifungal AFP Protein from *Aspergillus giganteus* Confers Resistance to the Blast Fungus Magnaporthe grisea in Transgenic Rice", Molecular Plant-Microbe Interactions, vol. 18, No. 9, pp. 960-972, XP002474393, Sep. 2005.
Gruener, Rose et al.:"The upstream region of the gene for the pathogenesis-related protein 1 a from tobacco responds to environmental as well as to developmental signals in transgenic plants", European Journal of Biochemistry, Berlin, Germany, vol. 220, No. 1, pp. 247-255, XP008023965, 1994.
Subramaniam, K. et al.:"Isolation of two differentially expressed wheat ACC synthase cDNAs and the characterization of one of their genes with root-predominant expression", Plant Molecular Biology, Springer, Dordrecht, NL, vol. 31, pp. 1009-1020, XP000619426, 1996.

* cited by examiner

*Primary Examiner* — Li Zheng
(74) *Attorney, Agent, or Firm* — Patent Central LLC; Stephan A. Pendorf

(57) ABSTRACT

The invention relates to a pathogen-inducible synthetic promoter which is suitable for regulating the transcription of a nucleic acid, and includes a minimal promoter, characterized in that the minimal promoter includes a sequence motif a) dbrmwa or b) twccmt which is disposed downstream from a TATA region and in front of a transcription starting point which is located on the minimal promoter and at which transcription of the nucleic acid to be regulated starts.

21 Claims, 9 Drawing Sheets

SEQUENCE LISTING

```
<160> NUMBER OF SEQ ID NOS: 15

<210> SEQ ID NO 1
<211> LENGTH: 69
<212> TYPE: DNA
<213> ORGANISM: Nicotiana plumbaginifolia
<220> FEATURE:
<221> NAME/KEY: misc_feature
<222> LOCATION: (1)..(8)
<223> OTHER INFORMATION: PstI Recognition Sequence
<220> FEATURE:
<221> NAME/KEY: TATA_signal
<222> LOCATION: (19)..(24)
<220> FEATURE:
<221> NAME/KEY: misc_feature
<222> LOCATION: (32)..(37)
<223> OTHER INFORMATION: dbrmwa
<220> FEATURE:
<221> NAME/KEY: misc_feature
<222> LOCATION: (62)..(69)
<223> OTHER INFORMATION: XhoI Recognition Sequence

<400> SEQUENCE: 1
aactgcagtg ggctcttgat atatcagctc ttcacaaacc ctagcagtct ctttctctcc    60
tctcgagtt                                                            69

<210> SEQ ID NO 2
<211> LENGTH: 67
<212> TYPE: DNA
<213> ORGANISM: Nicotiana plumbaginifolia
<220> FEATURE:
<221> NAME/KEY: misc_feature
<222> LOCATION: (1)..(8)
<223> OTHER INFORMATION: PstI Recognition Sequence
<220> FEATURE:
<221> NAME/KEY: TATA_signal
<222> LOCATION: (19)..(24)
<220> FEATURE:
<221> NAME/KEY: misc_feature
<222> LOCATION: (31)..(36)
<223> OTHER INFORMATION: dbrmwa
<220> FEATURE:
<221> NAME/KEY: misc_feature
<222> LOCATION: (60)..(67)
<223> OTHER INFORMATION: XhoI Recognition Sequence

<400> SEQUENCE: 2
aactgcagta aagccattta tatacactta gtgcaaagcc catgaaactc aagcctcaac    60
tcgagtt                                                              67

<210> SEQ ID NO 3
<211> LENGTH: 67
<212> TYPE: DNA
<213> ORGANISM: Nicotiana tabacum
<220> FEATURE:
<221> NAME/KEY: Misc_feature
<222> LOCATION: (1)..(8)
<223> OTHER INFORMATION: PstI Recognition Sequence
<220> FEATURE:
<221> NAME/KEY: TATA_signal
<222> LOCATION: (18)..(25)
<220> FEATURE:
<221> NAME/KEY: Misc_feature
```

```
<222> LOCATION: (33)..(38)
<223> OTHER INFORMATION: dbrmwa
<220> FEATURE:
<221> NAME/KEY: Misc_feature
<222> LOCATION: (60)..(67)
<223> OTHER INFORMATION: XhoI Recognition Sequence

<400> SEQUENCE: 3
aactgcagcc ttatcattat atatagggtg gtgggcaact atgcaatgac catattggac     60
tcgagtt                                                              67

<210> SEQ ID NO 4
<211> LENGTH: 69
<212> TYPE: DNA
<213> ORGANISM: Nicotiana tabacum
<220> FEATURE:
<221> NAME/KEY: misc_feature
<222> LOCATION: (1)..(8)
<223> OTHER INFORMATION: PstI Recognition Sequence
<220> FEATURE:
<221> NAME/KEY: TATA_signal
<222> LOCATION: (24)..(31)
<220> FEATURE:
<221> NAME/KEY: misc_feature
<222> LOCATION: (38)..(43)
<223> OTHER INFORMATION: dbrmwa
<220> FEATURE:
<221> NAME/KEY: misc_feature
<222> LOCATION: (62)..(69)
<223> OTHER INFORMATION: XhoI Recognition Sequence

<400> SEQUENCE: 4
aactgcagca gtttaatgta cattacatat aggttgcgga aaagtatata tatgctcaag     60
actcgagtt                                                            69

<210> SEQ ID NO 5
<211> LENGTH: 67
<212> TYPE: DNA
<213> ORGANISM: Nicotiana tabacum
<220> FEATURE:
<221> NAME/KEY: misc_feature
<222> LOCATION: (1)..(8)
<223> OTHER INFORMATION: PstI Recognition Sequence
<220> FEATURE:
<221> NAME/KEY: TATA_signal
<222> LOCATION: (19)..(24)
<220> FEATURE:
<221> NAME/KEY: misc_feature
<222> LOCATION: (31)..(36)
<223> OTHER INFORMATION: dbrmwa
<220> FEATURE:
<221> NAME/KEY: misc_feature
<222> LOCATION: (60)..(67)
<223> OTHER INFORMATION: XhoI Recognition Sequence

<400> SEQUENCE: 5
aactgcagta aagccattta tatacactta gtgcaaagcc catgaaactc aagcctcaac     60
tcgagtt                                                              67

<210> SEQ ID NO 6
<211> LENGTH: 67
<212> TYPE: DNA
<213> ORGANISM: Solanum tuberosum
<220> FEATURE:
<221> NAME/KEY: misc_feature
<222> LOCATION: (1)..(8)
<223> OTHER INFORMATION: PstI Recognition Sequence
<220> FEATURE:
<221> NAME/KEY: TATA_signal
<222> LOCATION: (24)..(30)
```

```
<220> FEATURE:
<221> NAME/KEY: misc_feature
<222> LOCATION: (38)..(43)
<223> OTHER INFORMATION: dbrmwa

<400> SEQUENCE: 6
aactgcagag tcaaatataa ttttatatta gaataattga atagtcaaac aagaaacttt      60
aacgagt                                                               67

<210> SEQ ID NO 7
<211> LENGTH: 75
<212> TYPE: DNA
<213> ORGANISM: Solanum tuberosum
<220> FEATURE:
<221> NAME/KEY: misc_feature
<222> LOCATION: (1)..(8)
<223> OTHER INFORMATION: PstI Recognition Sequence
<220> FEATURE:
<221> NAME/KEY: TATA_signal
<222> LOCATION: (26)..(34)
<220> FEATURE:
<221> NAME/KEY: misc_feature
<222> LOCATION: (36)..(41)
<223> OTHER INFORMATION: dbrmwa
<220> FEATURE:
<221> NAME/KEY: misc_feature
<222> LOCATION: (68)..(75)
<223> OTHER INFORMATION: XhoI Restriction Clevage Site

<400> SEQUENCE: 7
aactgcagac catgcaaagt gaaataaat aattcatact aagtagtgag agcaaagaag       60
aaaaaagctc gagtt                                                      75

<210> SEQ ID NO 8
<211> LENGTH: 69
<212> TYPE: DNA
<213> ORGANISM: Triticum aestivum
<220> FEATURE:
<221> NAME/KEY: promoter
<222> LOCATION: (1)..(69)
<223> OTHER INFORMATION: Minimalpromotor
<220> FEATURE:
<221> NAME/KEY: TATA_signal
<222> LOCATION: (13)..(20)
<220> FEATURE:
<221> NAME/KEY: misc_feature
<222> LOCATION: (38)..(44)
<223> OTHER INFORMATION: twcccmt

<400> SEQUENCE: 8
gcgccacgaa tctataaata ggcaccaacg agcagcttac ccattcatct ccctccctcc      60
ctccgccag                                                             69

<210> SEQ ID NO 9
<211> LENGTH: 149
<212> TYPE: DNA
<213> ORGANISM: Triticum aestivum
<220> FEATURE:
<221> NAME/KEY: TATA_signal
<222> LOCATION: (17)..(23)
<220> FEATURE:
<221> NAME/KEY: misc_feature
<222> LOCATION: (42)..(48)
<223> OTHER INFORMATION: twcccmt
<220> FEATURE:
<221> NAME/KEY: 5'UTR
<222> LOCATION: (51)..(149)
```

```
<400> SEQUENCE: 9
atctgcaggc gctgcctatt taatcccttc ccctccctcc attcccctcc aagaagagcc      60
acagcttcat ctgcagctac agctcctctt cgtcttcgac acacaagtat tttttcagga     120
caaagatcaa tccagataca catacacct                                        149

<210> SEQ ID NO 10
<211> LENGTH: 31
<212> TYPE: DNA
<213> ORGANISM: Petroselinum crispum
<220> FEATURE:
<221> NAME/KEY: enhancer
<222> LOCATION: (1)..(31)
<223> OTHER INFORMATION: BoxD

<400> SEQUENCE: 10
tacaattcaa acattgttca aacaaggaac c                                      31

<210> SEQ ID NO 11
<211> LENGTH: 128
<212> TYPE: DNA
<213> ORGANISM: Petroselinum crispum
<220> FEATURE:
<221> NAME/KEY: enhancer
<222> LOCATION: (1)..(128)
<223> OTHER INFORMATION: synthetic enhancement comprised of dimer of
      BoxS and BoxD
<220> FEATURE:
<221> NAME/KEY: enhancer
<222> LOCATION: (1)..(25)
<223> OTHER INFORMATION: BoxS
<220> FEATURE:
<221> NAME/KEY: enhancer
<222> LOCATION: (31)..(55)
<223> OTHER INFORMATION: BoxS
<220> FEATURE:
<221> NAME/KEY: enhancer
<222> LOCATION: (61)..(91)
<223> OTHER INFORMATION: BoxD
<220> FEATURE:
<221> NAME/KEY: enhancer
<222> LOCATION: (98)..(128)
<223> OTHER INFORMATION: BoxD

<400> SEQUENCE: 11
cagccaccaa acaggaccca gaattctagt cagccaccaa agaggaccca gaattctagt      60
tacaattcaa acattgttca aacaaggaac ctctagttac aattcaaaca ttgttcaaac     120
aaggaacc                                                              128

<210> SEQ ID NO 12
<211> LENGTH: 118
<212> TYPE: DNA
<213> ORGANISM: Solanum tuberosum
<220> FEATURE:
<221> NAME/KEY: enhancer
<222> LOCATION: (1)..(118)
<223> OTHER INFORMATION: synthetisc enhancer element of a tetramer of
      the Gst1 element
<220> FEATURE:
<221> NAME/KEY: enhancer
<222> LOCATION: (1)..(25)
<223> OTHER INFORMATION: BoxGst1
<220> FEATURE:
<221> NAME/KEY: enhancer
<222> LOCATION: (32)..(56)
<223> OTHER INFORMATION: BoxGst1
<220> FEATURE:
<221> NAME/KEY: enhancer
<222> LOCATION: (63)..(87)
```

<223> OTHER INFORMATION: BoxGst1
<220> FEATURE:
<221> NAME/KEY: enhancer
<222> LOCATION: (94)..(118)
<223> OTHER INFORMATION: BoxGst1

<400> SEQUENCE: 12
ttctagccac cagatttgac caaactctag tttctagcca ccagatttga ccaaactcta    60
gtttctagcc accagatttg accaaactct agtttctagc caccagattt gaccaaac    118

<210> SEQ ID NO 13
<211> LENGTH: 202
<212> TYPE: DNA
<213> ORGANISM: artificial sequence
<220> FEATURE:
<221> NAME/KEY: enhancer
<222> LOCATION: (1)..(202)
<223> OTHER INFORMATION: synthetic enhancer element comprised of dimer
      of BoxS and tetramer of BoxD
<220> FEATURE:
<221> NAME/KEY: enhancer
<222> LOCATION: (1)..(25)
<223> OTHER INFORMATION: Box S
<220> FEATURE:
<221> NAME/KEY: enhancer
<222> LOCATION: (31)..(55)
<223> OTHER INFORMATION: Box S
<220> FEATURE:
<221> NAME/KEY: enhancer
<222> LOCATION: (61)..(91)
<223> OTHER INFORMATION: Box D
<220> FEATURE:
<221> NAME/KEY: enhancer
<222> LOCATION: (98)..(128)
<223> OTHER INFORMATION: Box D
<220> FEATURE:
<221> NAME/KEY: enhancer
<222> LOCATION: (135)..(165)
<223> OTHER INFORMATION: Box D
<220> FEATURE:
<221> NAME/KEY: enhancer
<222> LOCATION: (172)..(202)
<223> OTHER INFORMATION: Box D

<400> SEQUENCE: 13
cagccaccaa agaggaccca gaattctagt cagccaccaa agaggaccca gaattctagt    60
tacaattcaa acattgttca aacaaggaac ctctagttac aattcaaaca ttgttcaaac   120
aaggaacctc tagttacaat tcaaacattg ttcaaacaag gaacctctag ttacaattca   180
aacattgttc aaacaaggaa cc                                            202

<210> SEQ ID NO 14
<211> LENGTH: 188
<212> TYPE: DNA
<213> ORGANISM: artificial sequence
<220> FEATURE:
<221> NAME/KEY: enhancer
<222> LOCATION: (1)..(188)
<223> OTHER INFORMATION: synthetic
<220> FEATURE:
<221> NAME/KEY: enhancer
<222> LOCATION: (1)..(25)
<223> OTHER INFORMATION: BoxS
<220> FEATURE:
<221> NAME/KEY: enhancer
<222> LOCATION: (31)..(55)
<223> OTHER INFORMATION: BoxS
<220> FEATURE:
<221> NAME/KEY: enhancer
<222> LOCATION: (61)..(85)
<223> OTHER INFORMATION: BoxS
<220> FEATURE:

```
<221> NAME/KEY: enhancer
<222> LOCATION: (91)..(115)
<223> OTHER INFORMATION: BoxS
<220> FEATURE:
<221> NAME/KEY: enhancer
<222> LOCATION: (121)..(151)
<223> OTHER INFORMATION: BoxD
<220> FEATURE:
<221> NAME/KEY: enhancer
<222> LOCATION: (158)..(188)
<223> OTHER INFORMATION: BoxD

<400> SEQUENCE: 14
cagccaccaa agaggaccca gaattctagt cagccaccaa agaggaccca gaattctagt      60
cagccaccaa agaggaccca gaattctagt cagccaccaa agaggaccca gaattctagt     120
tacaattcaa acattgttca aacaaggaac ctctagttac aattcaaaca ttgttcaaac     180
aaggaacc                                                              188

<210> SEQ ID NO 15
<211> LENGTH: 130
<212> TYPE: DNA
<213> ORGANISM: artificial sequence
<220> FEATURE:
<221> NAME/KEY: enhancer
<222> LOCATION: (1)..(130)
<223> OTHER INFORMATION: synthetic enhancer element comprised of the
      dimer of Gst1-Box and the Dimer of BoxD
<220> FEATURE:
<221> NAME/KEY: enhancer
<222> LOCATION: (1)..(25)
<223> OTHER INFORMATION: Box Gst1
<220> FEATURE:
<221> NAME/KEY: enhancer
<222> LOCATION: (32)..(56)
<223> OTHER INFORMATION: Box Gst1
<220> FEATURE:
<221> NAME/KEY: enhancer
<222> LOCATION: (63)..(93)
<223> OTHER INFORMATION: Box D
<220> FEATURE:
<221> NAME/KEY: enhancer
<222> LOCATION: (100)..(130)
<223> OTHER INFORMATION: Box D

<400> SEQUENCE: 15
ttctagccac cagatttgac caaactctag tttctagcca ccagatttga ccaaactcta      60
gttacaattc aaacattgtt caaacaagga acctctagtt acaattcaaa cattgttcaa     120
acaaggaacc                                                            130
```

PATHOGEN-INDUCIBLE SYNTHETIC PROMOTER

BACKGROUND OF THE INVENTION

Field of the invention

The present invention relates to a pathogen-inducible synthetic promoter which is suitable for regulating the transcription of a nucleic acid and includes a minimal promoter. Further, the present invention relates to a transgenic plant cell as well as transgenic plants. The present invention further concerns a process for producing a pathogen resistant plant.

Description of the Related Art

Various processes are known for creating plants which are resistant against pathogens such as fungi, virus, bacteria and nematodes. One of these processes employs the hypersensitive reaction (HR) of the plant, wherein the development of necrosis occurs at the location of direct contact between pathogen and plant. As a consequence of the HR a broad spectrum of pathogen defense mechanisms are triggered in adjacent cells, which prevent the further propagation of the pathogen in the plant tissue.

The HR can occur after expression of effector genes, such as for example avirulence genes of the pathogen and interaction with the product of a corresponding resistance gene (R-gene). The R-gene can herein already be present in the plant or, as the case may be, may be introduced by gene technology methods into the respective plant genome (Stuiver et al. 1998, Keller et al., 1999, Belbahri et al., 2001). Besides this, an over-expression or autoactivation of R-genes can lead to triggering of a HR (Tao et al., 2000, Tang et al., 1999, Bendahmane et al., 2002, Howles et al., 2005). By the over-expression of a R-gene a threshold is exceeded, which leads to initiation of a signal cascade, which conventionally is only initiated upon the presence of the pathogen or as the case may be the avirulence gene product. By triggering or activating this cascade a broad effective pathogen resistance can be achieved (Oldroyd and Staskawicz, 1998, Tang et al., 1999, Tao et al., 2000, Howles et al., 2005). Those R-genes are characterized as autoactive R-genes which are modified to the extent that for initiation of the signal cascade the presence of the pathogen/avirulence gene product is not necessary and at the same time, a reduced level of expression in comparison to the non-modified form is sufficient in order to achieve initiation of the signal cascade.

Stuiver et al. (1998) were able to show that the transformation of the avr9-gene from the phytopathogenic fungi *Cladosporium fulvum* under the control of the pathogen inducible Gst1-promoter from the potato in tomato plants, which carry the corresponding Cf9-gene, brought about a broad effective fungi resistance. A resistance against the oomycete *Phytophthora parasitica* var *nicotianae* could be achieved in *Nicotiana tabacum* after either the elicitor cryptogen from *P. cryptogea* or the bacterial elicitor popA from the phytopathogenic bacterium *Ralstonia solanacearum* was transformed in *N. tabacum*. Both genes were under the control of the pathogen inducible promoter hsr203J from *N. tabacum* (Keller et al., 1999, Belbahri et al., 2001).

The system of the HR triggering requires a stringent control of the expression of the effector gene at the location of the infection. In the case of uncontrolled expression, the expression of the effector gene causes negative effects on plant growth and therewith on the harvesting of horticultural plants (Stuiver and Custers, 2001). A controlled expression can however occur by the selection of suitable pathogen inducible promoters. These should, however, no expression or only a small expression under conditions of non-infestation, however, in the case of infection, cause a significantly higher expression at the location of the infection. After transformation from two different autoactive forms of the L6 rust resistance gene from flax (*Linum usitatissimum*) in flax under the control of the natural Fis1 promoters inducible by rust from flax, two phenotypes could be observed. On the one hand, normal growth plants, which showed no improved resistance against pathogens, and on the other hand, dwarf plants, with a broad pathogen resistance (Howles et al., 2005). These results show that, depending upon the employed form of the autoactive R-gene, the result could be a promoter activity which already lies above the threshold for induction of the signal cascade, while in the phenotypically unremarkable plants the induction of the Fis1-promoters is not sufficient in order to achieve this threshold. The specificity of the natural Fis1-promoters thus is not sufficient in order to achieve the broad effective pathogen resistance without negative effects on the plant growth.

Natural pathogen inducible promoters frequently show a non-specific activity and are activated by numerous stimuli, so that their use for the expression of the above-described effector genes is not practical, since a HR-triggering could also occur under non-infection conditions. This "leakiness" of the promoters leads to an impairment of plant growth and thus to a reduction of the harvest yield of horticultural crops. For this reason synthetic promoters were developed, which contain the sequence motives (cis-regulatory elements) from natural, pathogen inducible promoters, which are relevant for pathogen induction. Sequence motives for other stimuli are, in contrast, removed. The cis-regulatory elements are cloned upstream of the minimal promoter, whereby a functional promoter is produced, which exhibits an elevated specificity in comparison to the natural promoters, which were isolated from the respective cis-regulatory elements (Rushton et al., 2002). As minimal promoter for dicotyledonous plants the region −46 through +8 of the 35S-gene of the Cauliflower Mosaic Virus was employed. Besides this, the use of a minimal promoter from a natural promoter, out of which the respective cis-regulatory element was cloned, are known (Perl-Treves et al., 2004). For monocotyledonous plants, the use of the minimal promoter from the Act1-gene of rice is described (Lü et al., 2000).

Although the described synthetic promoters are an improvement over the natural promoters, these however show background activity even under non-infection conditions. These background activities vary among individual plant types. Thus, in all plant types examined until now a pathogen inducibility could be determined, however the strength of the induction and the absolute activity of the promoters vary. In the case of a too-strong background activity in non-infected tissue, then, only a small pathogen inducibility could be determined as quotient of the promoter activity in the infected tissue divided by the promoter activity in the non-infected tissue.

Until now, only the employed cis-regulatory elements were considered responsible for the level of the background activity of a synthetic promoter. These have a large influence on the strength of the promoter (Rushton et al., 2002). Little investigated until now was the influence of the minimal promoter. According to the literature the minimal promoter has only a very small influence on the regulation of the promoter activity (Singh, 1998). Bhuliar et al. (2003) could however detect a clear reduction of the promoter activity of the 35S-promoter when the minimal promoter (−46 through +1) was exchanged with heterologous plant minimal promoters. These differences lead back to the different sequences of the TATA-boxes, while, according to their opinion, the flanking regions of the TATA-box of the minimal promoter are not relevant for the promoter activity.

It is thus the task of the present invention to provide a pathogen inducible synthetic promoter with a small background activity.

BRIEF SUMMARY OF THE INVENTION

In accordance with the invention the solution of the task is accomplished by a pathogen inducible synthetic promoter with a minimal promoter, wherein the minimal promoter includes a sequence motive
a) dbrmwa or
b) twcccmt
which is situated downstream of a TATA-region and ahead of a transcription point laying on the minimal promoter at which the transcription of the nucleic acid to be regulated starts. Therein the sequence motive dbrmwa is suited primarily for dicots and the sequence motive twcccmt for monocot plants.

BRIEF DESCRIPTION OF THE SEVERAL VIEWS OF THE DRAWINGS

The invention is explained in more detail below with reference to the drawing in which.

DETAILED DESCRIPTION OF THE INVENTION

Figure 1:
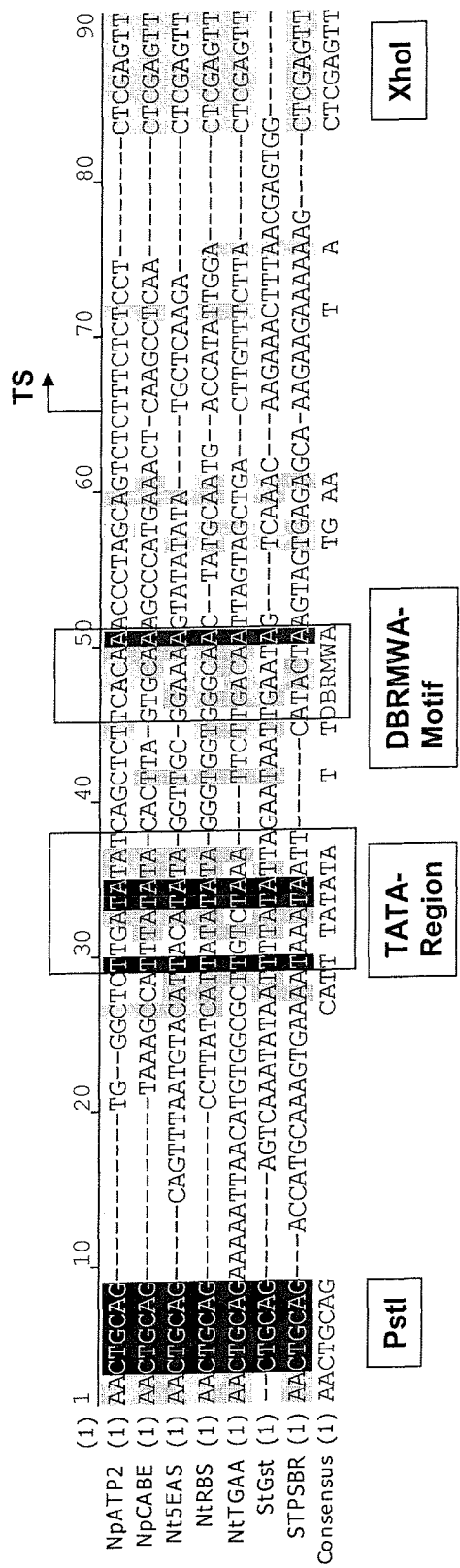
FIG. 1 shows a sequence comparison between the preferred minimal promoters for dicotyledonous plants with the conserved TATA-regions and the dbrmwa-motives as well as the cleavage site PstI and XhoI employed for cloning in the plasmid pMS231uc+.

The symbols of the sequence motive as used herein have the following meaning:
d=nucleotide a or g or t/u
b=nucleotide c or g or t/u
r=nucleotide g or a
m=nucleotide a or c
w=nucleotide a or t/u
a=nucleotide a
t=nucleotide t
c=nucleotide c In the sense of the invention a "minimal promoter" is a DNA-sequence of the promoter, which is necessary for promoter function. General transcription factors such as for example TFII-D, TFII-A, TFII-B, TFII-E and TFII-F could bond at this DNA-sequence, and form the platform for the bonding of the RNA-polymerase 11/TFII-F complex. Since the transcription of the DNA into the mRNA starts in this region, the transcription start point (TS) lies within the minimal promoter and is identified as position +1. The minimal promoter encompasses the TS and can extend for example from position −50 through position +15. Frequently a so-called TATA-box is found at the position −30, which however does not occur in all promoters. The TATA-box is a region of a sequence of thymine and adenine bases. The TATA-box is the binding location for the TATA-box binding protein (TBP).

Characterized as "synthetic promoters" are those promoters which do not occur in nature, are assembled from multiple elements and contain a minimal promoter as well as, upstream of the minimal promoter, at least one cis-regulatory element, which serves as the bonding location for special transcription factors. Synthetic promoters are designed according to the desired requirements and are induced or repressed by various factors.

"Derivatives" of a promoter are shortened or lengthened or partially identical versions of this promoter or homologs with the same, modified or singular characteristics. The expression "homology" herein means a homology of at least 70% based on DNA, which can be determined by known processes, for example, a computer supported sequence comparison (Altschul, S. F. et al., 1990).

The inventive pathogen inducible synthetic promoter results after transient biologic transformation in a reduced base activity in the leaf tissue of the respective plants in comparison to conventionally employed promoters with a minimal promoter such as the 35S-minimal promoter in dicotyledonous, and the corn-ubi1-minimal promoter in monocotyledonous, plants. Beyond this it was discovered that in the inventive pathogen inducible synthetic promoters the induction rate is also higher.

The inventive pathogen inducible synthetic promoters can thus be employed for production of transgenic plants which have a broad resistance against numerous pathogens, such as fungi, oomycetes, bacteria, virus, insects and nematodes.

The sequence motives dbrmwa and twcccmt lie in sense orientation on the codogenic strand between the TATA-box and the transcription start point and can also occur two or more times. Preferred sequences for minimal promoters are indicated in SEQ ID NOS: 1 through 9.

Cis-regulatory elements for production of pathogen inducible synthetic promoters are primarily those elements which occur in natural pathogen inducible promoters and they are responsible for pathogen induction. Their identification is described in Rushton et al. (2002).

Preferred cis-regulatory elements for production of synthetic promoters with use of the inventive minimal promoters are also described in WO 00/29592. From the cis-regulatory elements mentioned there, the D-box (SEQ ID NO: 10) is particularly suitable, in particular in the combination 2xS/2xD (SEQ ID NO: 11), as well as the Gst1-element, preferably in the combination 4xGst1 (SEQ ID NO: 12).

Preferred cis-element combinations include in general combinations of the D-box (SEQ ID NO: 10) with the S-box or, as the case may be, the Gst1-element. Particularly preferred are, besides the above-mentioned combination 2×S/2×D (SEQ ID NO: 11), the combination 2×S/4×D (SEQ ID NO: 13); 4×S/2×D (SEQ ID NO: 14) and 2Gst1/2×D (SEQ ID NO: 15). The combination of the 2×S/4×D element (SEQ ID NO: 13) with the minimal promoter according to SEQ ID NO: 2 shows in transgenic potatoes following infection with *Phytophthora infestans* an average elevation of the reporter gene activity by a factor of 253,000 in comparison to a non-infected control.

If the element 4×S/2×D (SEQ ID NO: 14) was cloned ahead of the minimal promoter (SEQ ID NO: 2), an average increase in the reporter gene activity by a factor of 2,892 could be detected. With element 2×Gst1/2×D (SEQ ID NO: 15) an average increase by a factor of 2,967 in comparison to control was achieved.

With the inventive promoters transgenic plant cells can be produced, which can be regenerated to complete plants with improved defensive characteristics against pathogens. The inventive promoters are likewise contained in the seeds of such transgenic plants. The invention is not limited to particular types of plants.

The present invention is thus concerned with the process for production of a plant resistant against pathogens, in which a gene suitable for production of a pathogen resistance is introduced into a plant cell, which is under the control of a pathogen inducible synthetic promoter, and subsequently this plant cell is regenerated into a plant, characterized in that the pathogen inducible synthetic promoter is a pathogen inducible synthetic promoter as described above.

EXAMPLES

FIG. 1 shows a sequence comparison between the preferred minimal promoters (SEQ ID NOS: 1 through 7) for dicotyledonous plants with the conserved TATA-regions and the dbrmwa-motives as well as the cleavage site PstI and XhoI employed for cloning in the plasmid pMS23luc+.

Figure 2:
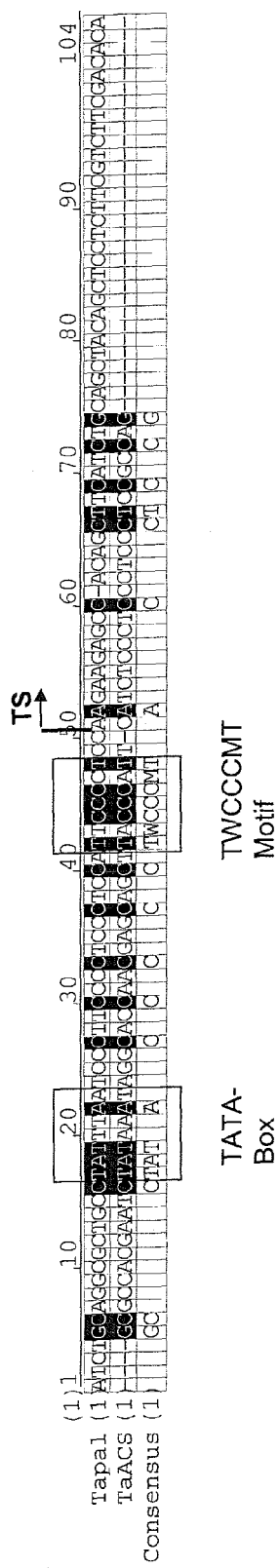
FIG. 2 shows a sequence comparison between the minimal promoters, preferred for monocotyledonous plants, which are employed for the transient transformation of wheat leaves, and the sequence motive twcccmt as conserved region.

FIG. 2 shows a sequence comparison between the minimal promoters (SEQ ID NOS: 8 and 9), preferred for monocotyledonous plants, which are employed for the transient transformation of wheat leaves. In addition to the TATA-region the sequence motive twcccmt is shown as conserved region.

It could be shown that the minimal promoters StGst (SEQ ID NO: 6), NtTGAA (SEQ ID NO: 5), StPSBR (SEQ ID NO: 7), NpCABE (SEQ ID NO: 2), NtRBS (SEQ ID NO: 3), NpATP2 (SEQ ID NO: 1) and Nt5EAS (SEQ ID NO: 4) exhibited a clearly reduced activity (<70%) in comparison to the 35S-minimal promoter.

Figure 3:
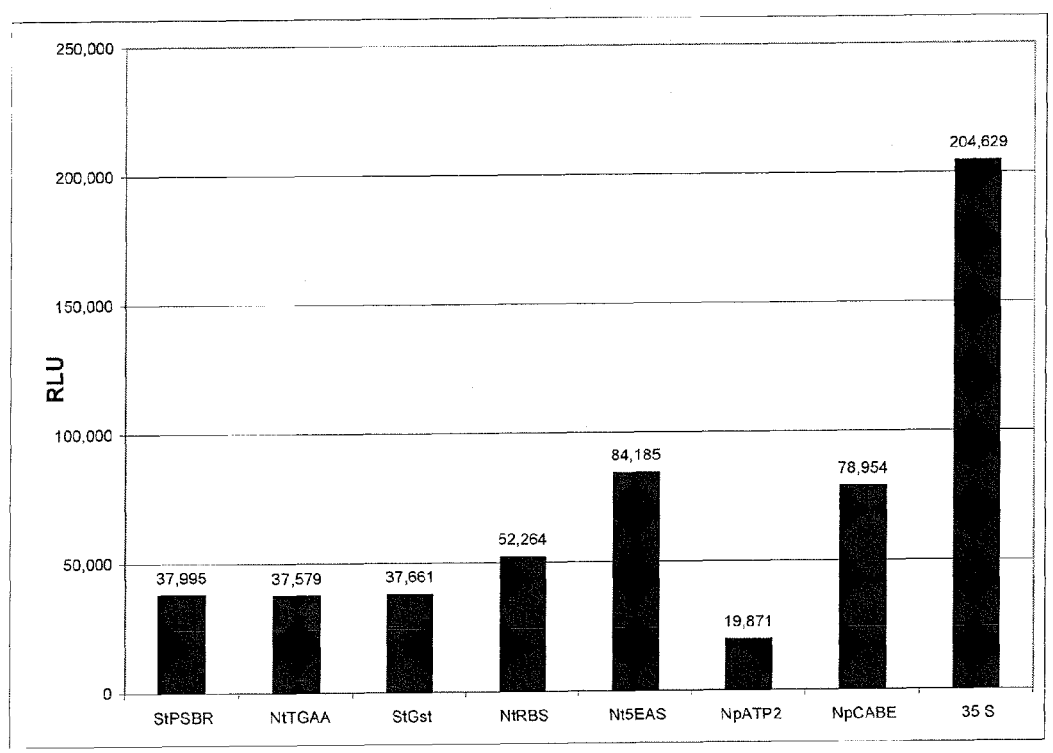
FIG. 3 shows an overview of the average reporter gene activity of non-infected, transgenic potato plants with a synthetic promoter comprised of the 4xGstI element and the indicated minimal promoters, cloned ahead of the luciferase gene from *Photinus pyralis* as reporter gene.

FIG. 3 shows an overview of the average reporter gene activity of non-infected, transgenic potato plants with a synthetic promoter comprised of the 4×Gst1 element (SEQ ID NO: 12) and the indicated minimal promoters, cloned ahead of the luciferase gene from *Photinus pyralis* as reporter gene (RLU=relative light unit). Stable, transgenic lines with the minimal promoters, which carry the sequence motive dbrmwa showed under controlled conditions a clearly reduced expression of the reporter gene in comparison to the 35S-minimal promoter. The smallest average activity was achieved with use of the minimal promoter of the NpATP2 gene (SEQ ID NO: 1). In these plants only 9.7% of the average activity of the 35S-minimal promoter could be measured. With use of the minimal promoters StPSBR (SEQ ID NO: 7), NtTGAA (SEQ ID NO: 5) or StGst (SEQ ID NO: 6) 18% of the activity of the 35S-minimal promoter was measured, with NtRBS-minimal promoter (SEQ ID NO: 3) 26%, with NpCABE-minimal promoter (SEQ ID NO: 2) 39% and with Nt5EAS-minimal promoter (SEQ ID NO: 4) 41%.

Figure 8:
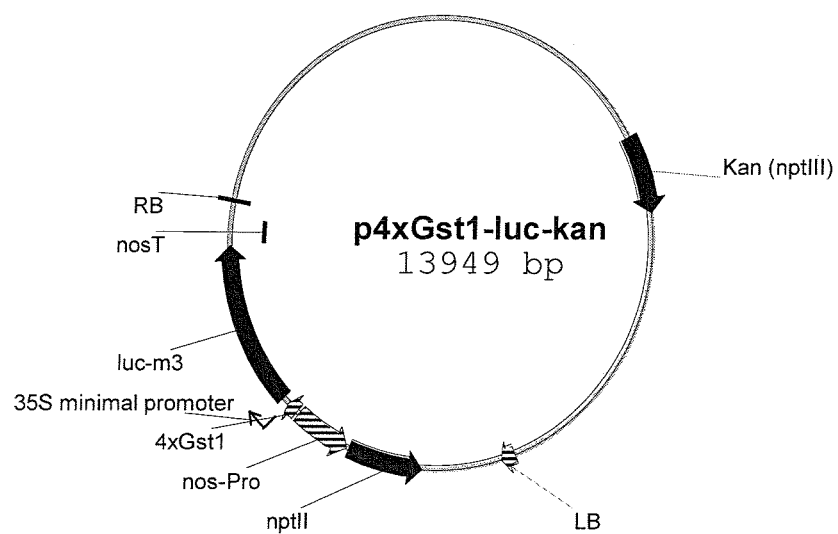

For the person of ordinary skill the manufacture of suitable constructs for transformation of plants with the inventive promoters is no problem. Thus for example the binary vectors p4×Gst1-luc-kan (FIG. 8) could be produced, which was used for the stable transformation of potato plants of the variety "Baltica". This vector is a derivative of the binary vector pGPTV (Becker et al., 1992). The binary vector p4×Gst1 luc-kan carries the luciferase gene from *Photinus pyralis* under the control of the synthetic promoter 4×Gst1:35 S minimal promoter (Rushton et al., 2002). As the termination sequence the plasmid is given the terminator of the nopalin-synthase gene from *Agrobacterium tumefaciens*. The described expression cassette is localized on the T-DNA together with a functional expression cassette for the neomycinphosphotransferase gene (nptII) as selection marker. The neomycinphosphotransferase imparts to the transgenic plants resistance against kanamycin or paromycin. In order to exchange the 35S-minimal promoter with the above-described minimal promoters, the binary vector p4×Gst1 luc-kan was digested with XhoI/SalI, whereby the 35S-minimal promoter was removed, the tetramer of the Gst1-element however remained intact. The SalI cleavage location was filled with the aid of the enzyme Klenow polymerase and dNTP's in order to achieve a blunt end. The minimal promoters, cloned in the plasmid pMS23luc+, were excised using PdiI/XhoI-digestion and ligated in the binary vector and subsequently transformed in *E. coli*. Binary vectors with the new sequence were transformed in the *Agrobacterium* type GV3101::pMP90 (Koncz and Schell, 1986) (An, 1987) and selected using the antibiotic kanamycin (50 mg/l). The transgenic *Agrobacterium* were employed for the transformation of potatoes of the type "Baltica" (Dietze et al., 1995).

Figure 4:
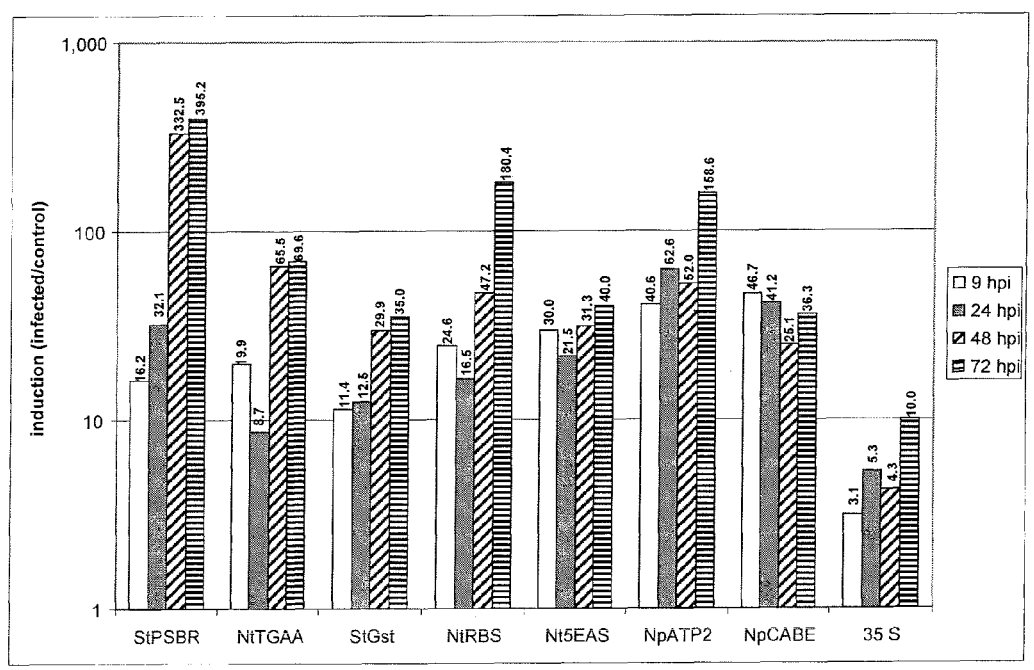
FIG. 4 shows a overview of the individual inductions following in vitro infection of stable, transgenic potato plants with the synthetic promoter comprised of the 4xGstI element and the indicated minimal promoters.

FIG. 4 shows a overview of the individual inductions following in vitro infection of stable, transgenic potato plants with the synthetic promoter comprised of the 4×Gst1 element (SEQ ID NO: 12) and the indicated minimal promoters. The infection occurred in in vitro plants with a zoospore suspension of *Phytophthora infestans*.

At various times following inoculation leaf samples of in vitro plants were removed, the sample weight was determined and 10 volumes IxCCLR buffer (Promega, Mannheim) was added. The material was homogenized with the aid of a RIA/90 Hnrnflga.ni$^{7}$'c'r OKA Labortechnik, Staufen) in buffer on ice. By centrifugation at >10,000 ×g for 10 minutes the homogenate was clarified and 10 pl of the supernatant was suspended with 50 pl of the substrate LAR (Promega, Mannheim) in a luminometer tube and the light emission was determined as value for the activity of the luciferase in the luminometer (Sirius, Berthold Detection System GmbH, Pforzheim). For control or comparison in vitro plants were employed, which were raised under the same conditions and, in place of zoospores, were subject to a sham treatment with water. The average value of the quotients, in 5 independent lines, of the luciferase activity of the infected to the sham treated variants, indicates the induction of the synthetic promoter by the infection. As can be seen in FIG. 4, with use of the 35S-minimal promoter, a maximal induction of the luciferase activity by a factor of only 10 could be achieved 72 hours after infection. All new minimal promoters in contrast showed a clearly improved induction. The strongest induction after infection with a factor 395 was achieved 72 hours post-infection with the StPSBR minimal promoter (SEQ ID NO: 7). In general, the induction by use of the new minimal promoters could be improved at time 72 hours post-induction by a factor of 3.5 with StGst minimal promoter (SEQ ID NO: 6) to a factor of 39.5 with StPSBR minimal promoter (SEQ ID NO: 7) in comparison to 35S-minimal promoter. Interestingly, clear differences in the kinetics of the induction following pathogen induction exist between the minimal promoters. While the most discernible induction is measurable with use of the 35S-minmal promoter 72 hours post induction, this also applies with use of the StPSBR, NtTGAA, StGst, NtRBS as well as NpATP2 minimal promoter. For NpCABE and Nt5EAS promoters in comparison a strong activation is already detectable at time interval 9 and the induction remains at approximately the achieved level over the remaining test period.

Figure 5:
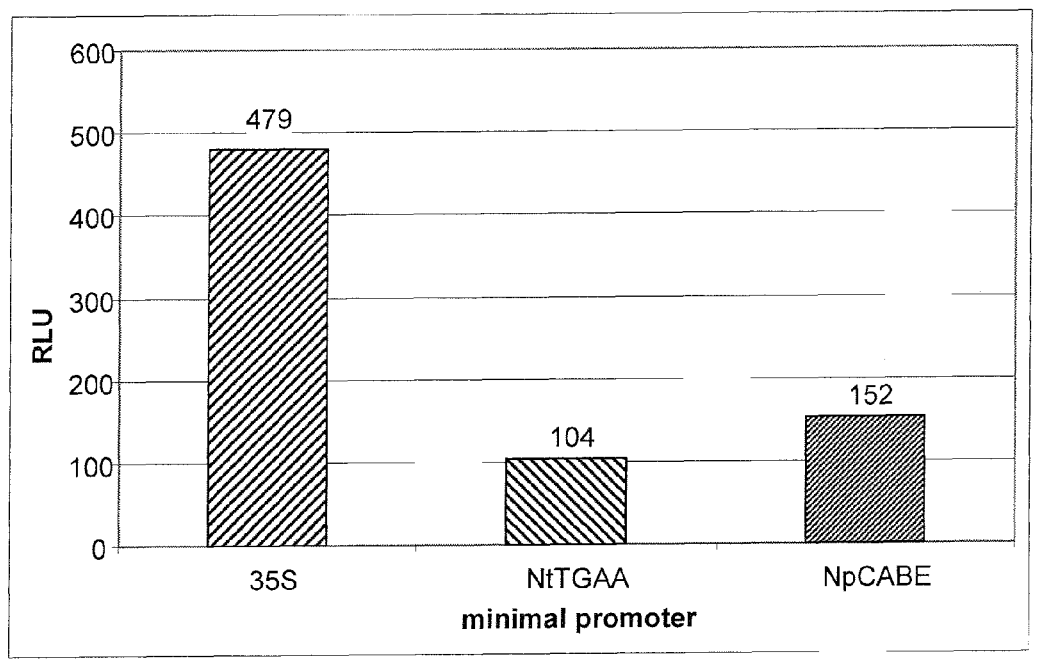
FIG. 5 shows that when transgenic sprouts were multiplied and inoculated under in vitro conditions with the zoospore suspension of *Phytophthora infestans*, also with use of the cis-regulatory element 2xS/2xD a reduced background activity could be achieved with the inventive minimal promoters in comparison to 35S-minimal promoters
Figure 6:
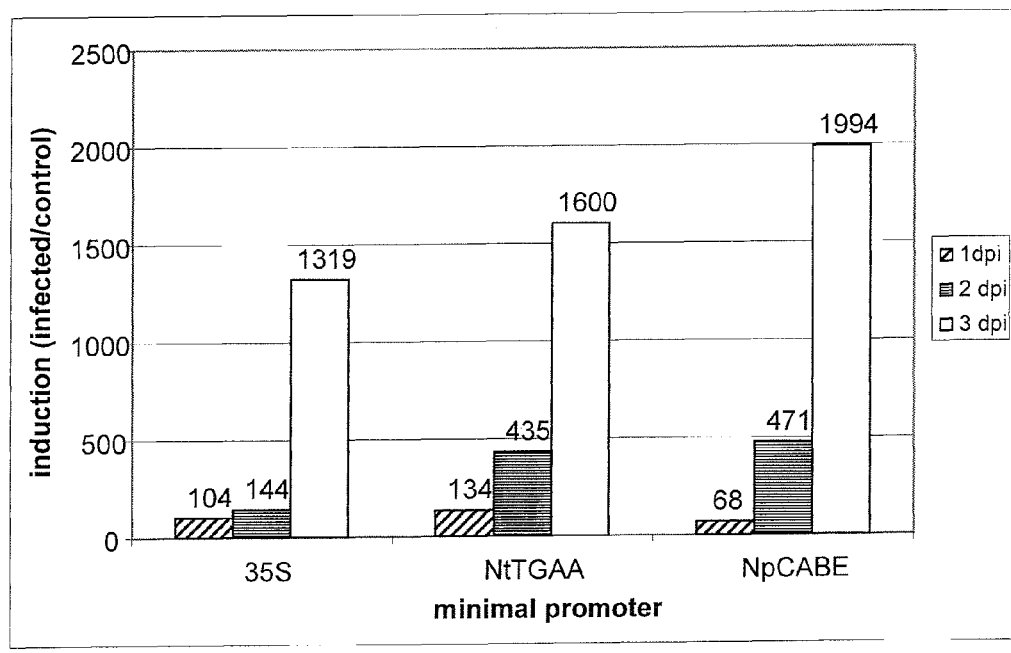
FIG. 6 shows that at the same time a stronger induction of the synthetic promoters following inoculation of the transgenic potatoes with *P. infestans* could be observed.

The preferability of the new minimal promoters was shown following fusion with the cis-element combination 2×S/2×D. For this, potato plants were stably transformed with the binary vectors p2×S/2×Dluc-kan, p2×S/2×DNpCABEiuc-kan and p2×S/2×DNtTGAAluc-kan. The binary vectors were produced in that the 4×Gst1-element from the above-described binary vector with the new minimal promoter and the 4×Gst1-element were eliminated via Bcul/Eco1471-digestion and the element 2×S/2×D (SEQ ID NO: 11) was introduced as Bcul/Eco321-fragment. Binary vectors with the new sequence were transformed in the Agrobacterium type GV3101::pMP90 (Koncz and Schell, 1986) (An, 1987) and selected using the antibiotic kanamycin (50 mg/l). The transgenic Agrobacterium were employed for the transformation of potato of the type "Baltica" (Dietze et al., 1995). Transgenic sprouts were multiplied and inoculated under in vitro conditions with the zoospore suspension (50,000 spores/ml) of Phytophthora infestans. It could be shown, that also with use of the cis-regulatory element 2×S/2×D (SEQ ID NO: 11) a reduced background activity could be achieved with the inventive minimal promoters in comparison to 35S-minimal promoters (FIG. 5). At the same time a stronger induction of the synthetic promoters following inoculation of the transgenic potatoes with P. infestans could be observed (FIG. 6). The amplification of the induction was not so pronounced at the later time (3 days post infection=3 dpi) as could be observed following use of the 4×Gst1-element. Two days following infection however by the use of the new minimal promoter a clearly stronger induction following pathogen attack could be observed. Herewith the use of these minimal promoters has as a consequence an improvement of the kinetics of the synthetic promoter, so that the reaction to pathogen attack occurs earlier, in comparison to the synthetic promoter using the 35S-minimal promoter.

Figure 7:
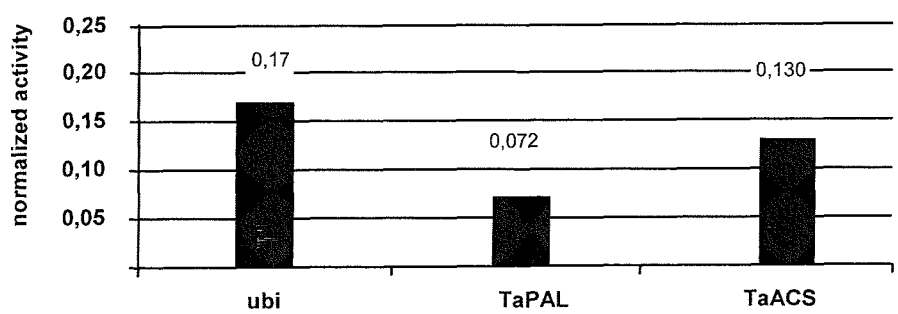
FIG. 7 shows a comparison of the normalized activity of pathogen inducible synthetic promoters comprised of an element 2xS/2xD and the minimal promoters ubil (comparison promoter), TaPAL and TaACS following biologic transformation in primary leaves of the wheat type "Taifun".

FIG. 7 shows a comparison of the normalized activity of pathogen inducible synthetic promoters comprised of an element 2×S/2×D (SEQ ID NO: 11) and the minimal promoters ubi1 (comparison promoter), TaPAL (SEQ ID NO: 9) and TaACS (SEQ ID NO: 8) following biologic transformation in primary leaves of the wheat type "Taifun". As can be seen, the new minimal promoters TaPAL and TaACS in wheat have a reduced base activity in comparison to ubi1-minimal promoter. While a normalized activity of 0.17 was measured with the ubi1-minimal promoter, with use of the TaPAL-minimal promoter this could be reduced to 0.072, and with use of the TaACS-minimal promoter it could be reduced to 0.13.

Figure 9:
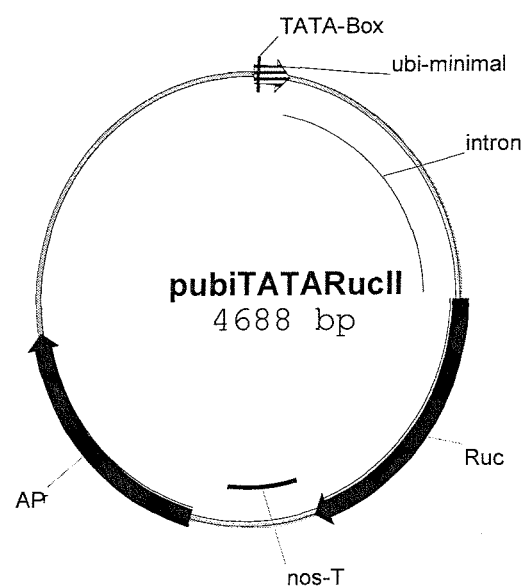

FIG. 9 shows the plasmid pubiTATARucII, which contains the cDNA with the luciferase gene from Renilla reniformis, as it exists in the commercially available plasmid pRL-Null. The cDNA is under the control of the ubi1-minimal promoter. The ubi1-minimal promoter includes the sequence range from −45 through +76 relative to the transcription start point. For elevating the expression strength the first intron of the ubi1-gene is maintained in its natural context in the plasmid ahead of the reporter gene. The plasmid serves for cloning the cis-regulatory element 2×S/2×D (SEQ ID NO: 11), in order thereby to produce a pathogen inducible synthetic promoter. The ubi1-minimal promoter was exchanged for the new minimal promoter for improving the characteristics of the synthetic promoter.

REFERENCES

An, G. (1987). Binary Ti vectors for plant transformation and promoter analysis. Methods Enzymol. 153: 292-305

Altschul, S. F. et al. (1990), Basic Local Alignment search tool, J. Mol. Biol. 215: 403-410

Becker, D. et al. (1992). New plant binary vectors with selectable markers located proximal to the left T-DNA border. Plant Mol Biol. 29: 1195-1 197

Belbahri, L. et al. (2001). A local accumulation of the Ralstonia solanacearum PopA protein in transgenic tobacco renders a compatible plant-pathogen interaction incompatible. Plant J. 28: 419-430

Bendahmane, A. et al. (2002). Constitutive gain-of-function mutants in a nucleotide binding site-leucine rich repeat protein encoded at the Rx locus of potato. Plant J. 32: 192-204

Bhullar, S. (2003). Strategies for the development of functionally equivalent Promoters with minimum sequence homology for transgenic expression in plants: cis-elements in a novel DNA context versus domain swapping. Plant Physiol. 132: 988-998

Dietze, J. et al. (1995). Agrobacterium-mediated transformation of potato (Solanum tuberosum). In: Gene Transfer to Plants XXII (Potrykus, I. and Spangenberg, G., eds.). Berlin: Springer Verlag, pp 24-29

Howles, P. et al. (2005). Autoactive alleles of the flax L6 rust resistance gene induce non-race-specific rust resistance associated with the hypersensitive response. Mol. Plant-Microbe Interact. 18: 570-582

Keller, H. et al. (1999). Pathogen-induced elicitin production in transgenic tobacco generates a hypersensitive response and non-specific disease resistance. Plant Cell11. 223-235

Koncz, C. and Schell, J. (1986). The promoter of TL-DNA gene 5 controls the tissue specific expression of chimeric genes carried by a novel type of Agrobacterium vector. Mol. Gen. Genet., 204: 383-396

Lü, H. et al. (2000). Construction of chimeric inducible Promoters by elicitors of rice fungal blast pathogen and their expression in transgenic rice. Chinese Science Bulletin 45: 242-246

Oldroyd, G. E. D. and Staskawicz, B J. (1998). Genetically engineered broad spectrum disease resistance in tomato. Proc. Natl. Acad. Sei. U.S.A. 95: 10300-10350

Maas, C. et al. (1991). The combination of a novel stimulatory element in the first exon of the maize Shrunken-1 gene with the following introni enhances reporter gene expression up to 1000-fold. Plant Mol Biol. 16: 199-207

Perl-Treves, R. et al. (2004). Early induction of the Arabidopsis GSTF8 Promoter by specific strains of the fungal pathogen Rhizactonia solani. Mol. Plant-Microbe Interact. 17: 70-80

Rushton, P J. et al. (2002). Synthetic plant promoters containing defined regulatory elements provide novel insights into pathogen- and wound-induced signaling. Plant Cell 14, 749-762

Singh, K. B. (1998). Transcriptional regulation in plants: the importance of combinatorial control. Plant Physiol. 118:

Stuiver, M. H. and Güsters, J. H. H. V. (2001). Engineering disease resistance in plants. Nature 4 11: 865-868

Stuiver, M. H. et al. (1998). Infection-induced expression of the avirulence gene avr9 in transgenic Cf9 tomato plants confers resistance to fungal pathogen attack. 7$^{th}$ International congress of plant pathology, 9-16 Aug., Edinburgh, Scotland Tang, X. et al. (1999). Overexpression of Pto activates defense responses and confers broad resistance. Plant Cell 11:15-29

Tao, Y. et al. (2000). Mutational analysis of the *Arabidopsis* nucleotide binding site-leucine-rich repeat resistance gene RPS2. Plant Cell 12: 2541-2554

The invention claimed is:

1. A pathogen inducible synthetic promoter for regulating the transcription of a nucleic acid, which includes at least one cis regulatory element and a minimal promoter, wherein the minimal promoter is heterologous to the at least one cis regulatory element, wherein the minimal promoter consists essentially of a TATA-box, a transcription starting point, and a sequence motif dbrmwa, and wherein the sequence motif dbrmwa is disposed downstream from the TATA-box and in front of the transcription starting point at which transcription of the nucleic acid to be regulated starts.

2. The pathogen inducible synthetic promoter according to claim 1, wherein the sequence motif occurs two or more times in the minimal promoter.

3. The pathogen inducible synthetic promoter according to claim 1, in which the minimal promoter includes the nucleotide sequence according to SEQ ID NO: 2 or derivatives thereof.

4. The pathogen inducible synthetic promoter according to claim 1, which includes in addition to the minimal promoter at least one cis-regulating element with the nucleotide sequence according to SEQ ID NO: 13.

5. A recombinant gene comprising the pathogen inducible synthetic promoter according to claim 1.

6. A plant cell, in which the pathogen inducible synthetic promoter according to claim 1 has been integrated into DNA of the plant cell.

7. A transgenic plant with a plant cell according to claim 6.

8. A seed of a transgenic plant comprising the pathogen inducible synthetic promoter according to claim 1.

9. A process for producing a pathogen resistant plant, comprising introducing into a plant cell a nucleic acid causing pathogen resistance, wherein the nucleic acid is under control of the pathogen inducible synthetic promoter according to claim 1, and subsequently regenerating a plant from the plant cell.

10. A vector or an expression cassette comprising a minimal promoter for producing a pathogen inducible synthetic promoter, wherein the minimal promoter consists essentially of a TATA-box, a transcription starting point, and a sequence motif dbrmwa, wherein the sequence motif dbrmwa is disposed downstream from the TATA-box and in front of the transcription starting point at which transcription of a nucleic acid to be regulated starts, and wherein the TATA-box is the binding location for the TATA-box binding protein (TBP) associated with transcription of said nucleic acid, and wherein the minimal promoter is operably linked to at least one cis regulatory element.

11. The vector or expression cassette according to claim 10, wherein the sequence motif occurs two or more times in the minimal promoter.

12. The vector or expression cassette according to claim 10, wherein the minimal promoter includes the nucleotide sequence according to one of SEQ ID NOS: 1-9 or derivatives thereof.

13. A pathogen inducible synthetic promoter, which is suitable for regulating the transcription of a nucleic acid, and includes at least one cis regulatory element and a minimal promoter,
wherein the minimal promoter is heterologous to the cis regulatory element,
wherein the minimal promoter consists essentially of a TATA-box, a transcription starting point, and a sequence motif dbrmwa,
wherein the sequence motif dbrmwa is disposed downstream from the TATA-box and in front of the transcription starting point at which transcription of the nucleic acid to be regulated starts, and
which includes, in addition to the minimal promoter, at least one cis-regulating element with the nucleotide sequence according to one of SEQ ID NOS: 10-15.

14. A plant cell, in which the expression cassette according to claim 10 has been integrated into DNA of the plant cell.

15. A transgenic plant comprising the plant cell according to claim 14.

16. A seed of a transgenic plant comprising the expression cassette according to claim 10.

17. A process for producing a pathogen resistant plant, comprising introducing in a plant cell a nucleic acid causing pathogen resistance, wherein the nucleic acid is the vector or the expression cassette according to claim 10, and subsequently regenerating a plant from the plant cell.

18. A pathogen inducible synthetic promoter for regulating the transcription of a nucleic acid, which includes at least one cis regulatory element and a minimal promoter, wherein the minimal promoter is heterologous to the at least one cis regulatory element and wherein the minimal promoter comprises a sequence motif dbrmwa which is disposed downstream from a TATA-box and in front of a transcription starting point which are located on the minimal promoter and at which transcription of the nucleic acid to be regulated starts, and wherein the TATA-box is the binding location for the TATA-box binding protein (TBP) associated with transcription of said nucleic acid.

19. The vector or expression cassette according to claim 10, wherein the minimal promoter is operably linked to a recombinant gene.

20. The vector or expression cassette according to claim 11, wherein the minimal promoter is operably linked to a recombinant gene.

21. The vector or expression cassette according to claim 12, wherein the minimal promoter is operably linked to a recombinant gene.

* * * * *